United States Patent
Ghodrati et al.

(10) Patent No.: US 11,559,362 B2
(45) Date of Patent: Jan. 24, 2023

(54) SYSTEMS AND METHODS FOR AUTONOMOUS CARDIAC MAPPING

(71) Applicant: Boston Scientific Scimed Inc., Maple Grove, MN (US)

(72) Inventors: Alireza Ghodrati, Hopkinton, MA (US); Leili Salehi, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 453 days.

(21) Appl. No.: 16/686,576

(22) Filed: Nov. 18, 2019

(65) Prior Publication Data

US 2020/0155250 A1 May 21, 2020

Related U.S. Application Data

(60) Provisional application No. 62/770,156, filed on Nov. 20, 2018.

(51) Int. Cl.
*A61B 34/32* (2016.01)
*A61B 34/20* (2016.01)
(Continued)

(52) U.S. Cl.
CPC .............. *A61B 34/32* (2016.02); *A61B 5/065* (2013.01); *A61B 34/20* (2016.02); *G06N 20/00* (2019.01);
(Continued)

(58) Field of Classification Search
CPC . A61B 2034/2068; A61B 34/20; A61B 34/32; A61B 5/065; A61B 5/318; A61B 6/481; A61B 6/504; A61B 2034/301; A61B 34/30; A61B 5/0538; A61B 5/6852; A61B 5/6869; A61B 5/6885; A61B 2018/00351; A61B 5/341; A61B 5/287;
(Continued)

(56) References Cited

U.S. PATENT DOCUMENTS 7,850,642 B2 12/2010 Moll et al.
8,046,049 B2 10/2011 Govari et al.
(Continued)

FOREIGN PATENT DOCUMENTS

WO WO-2014036439 A2 * 3/2014 ......... A61B 18/1492
WO 2017/115212 A1 7/2017

OTHER PUBLICATIONS

Rhythm: An Open Source Imaging Toolkit for Cardiac Panoramic Optical Mapping—2017 (Year: 2017).*
(Continued)

*Primary Examiner* — Nizar N Sivji
(74) *Attorney, Agent, or Firm* — Nelson Mullins Riley & Scarborough LLP

(57) ABSTRACT

Methods and systems for autonomous cardiac mapping are disclosed. An example system for autonomous cardiac mapping of a heart chamber includes a processor being configured to acquire a representative geometric shell of the heart chamber, control a robotic device to autonomously navigate a mapping probe to a plurality of locations within the heart chamber based at least in part on the representative geometric shell, and generate a three-dimensional electroanatomical map of the heart chamber based on electrical data collected by the probe at the plurality of locations.

16 Claims, 8 Drawing Sheets

(51) Int. Cl.
*G06N 20/00* (2019.01)
*A61B 5/06* (2006.01)

(52) U.S. Cl.
CPC ... *A61B 2034/2068* (2016.02); *G06T 2200/08* (2013.01); *G06T 2207/10081* (2013.01); *G06T 2207/10088* (2013.01); *G06T 2207/10132* (2013.01); *G06T 2207/20081* (2013.01); *G06T 2207/30048* (2013.01)

(58) Field of Classification Search
CPC .............. A61B 2560/029; G06N 20/00; G06T 2207/10081; G06T 2200/08; G06T 2207/30048; G06T 2207/30101; G06T 15/10; G06T 2207/10088; G06T 2207/10132; G06T 2207/20081
See application file for complete search history.

(56) References Cited

U.S. PATENT DOCUMENTS

| | | | |
|---|---|---|---|
| 9,204,935 B2 | 12/2015 | Hauck et al. | |
| 9,629,682 B2 | 4/2017 | Wallace et al. | |
| 2006/0058693 A1* | 3/2006 | Beatty | A61N 1/3625 600/508 |
| 2007/0197929 A1* | 8/2007 | Porath | A61B 5/287 600/509 |
| 2007/0198008 A1 | 8/2007 | Hauck et al. | |
| 2007/0299353 A1 | 12/2007 | Harlev et al. | |
| 2008/0058657 A1* | 3/2008 | Schwartz | A61B 5/0538 600/508 |
| 2009/0076476 A1* | 3/2009 | Barbagli | A61B 5/1076 600/587 |
| 2009/0105579 A1 | 4/2009 | Garibaldi | |
| 2009/0262109 A1* | 10/2009 | Markowitz | A61B 34/20 345/419 |
| 2010/0168550 A1* | 7/2010 | Byrd | A61B 5/063 600/407 |
| 2010/0256558 A1 | 10/2010 | Olson et al. | |
| 2010/0305429 A1* | 12/2010 | Shachar | A61B 5/06 600/424 |
| 2012/0065481 A1* | 3/2012 | Hunter | A61B 6/463 600/513 |
| 2012/0150021 A1* | 6/2012 | Schwartz | A61B 5/287 600/424 |
| 2013/0030280 A1* | 1/2013 | Govari | A61B 5/287 703/11 |
| 2013/0274582 A1* | 10/2013 | Afonso | A61B 5/065 600/374 |
| 2014/0194867 A1 | 7/2014 | Fish et al. | |
| 2015/0223757 A1* | 8/2015 | Werneth | A61B 5/6852 600/301 |
| 2016/0066814 A1* | 3/2016 | Markowitz | A61B 5/339 600/424 |
| 2016/0120426 A1* | 5/2016 | Urman | A61B 5/7485 600/424 |
| 2018/0228389 A1* | 8/2018 | Mahapatra | A61B 5/287 |
| 2019/0172211 A1* | 6/2019 | Novikov | A61B 6/032 |
| 2020/0029845 A1* | 1/2020 | Baram | G06N 3/04 |
| 2020/0214662 A1* | 7/2020 | Konofagou | A61B 5/339 |

OTHER PUBLICATIONS

Shape and Appearance Models for Automatic Coronary Artery Tracking—2008 (Year: 2008).*
NIH Public Access—Standardized Evaluation Methodology and Reference Database for Evaluating Coronary Artery Centerline Extraction Algorithms—2009 (Year: 2009).*
Electrocardiographic Textbooks Based on Template Hearts Warped Using Ultrasonic Images—2012 (Year: 2012).*
Coronary Centerline Extraction Using Multiple Hypothesis Tracking and Minimal Paths—2008 (Year: 2008).*
The Future of Cardiac Mapping—2012 (Year: 2012).*
International Search Report and Written Opinion received for PCT Patent Application No. PCT/US2019/061944, dated Feb. 6, 2020, 10 pages.

* cited by examiner

SYSTEMS AND METHODS FOR AUTONOMOUS CARDIAC MAPPING

CROSS-REFERENCE TO RELATED APPLICATION

This application claims priority to Provisional Application No. 62/770,156, filed Nov. 20, 2018, which is herein incorporated by reference in its entirety.

TECHNICAL FIELD

The present disclosure relates to medical systems and methods for mapping an anatomical space of the body. More specifically, the disclosure relates to systems and methods for cardiac mapping.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional three-dimensional (3D) mapping techniques include contact mapping and non-contact mapping, and may employ a combination of contact and non-contact mapping. In both techniques, one or more catheters are advanced into the heart. With some catheters, once in the chamber, the catheter may be deployed to assume a 3D shape. In contact mapping, physiological signals resulting from the electrical activity of the heart are acquired with one or more electrodes located at the catheter distal tip after determining that the tip is in stable and steady contact with the endocardium surface of a particular heart chamber. In non-contact-based mapping systems, using the signals detected by the non-contact electrodes and information on chamber anatomy and relative electrode location, the system provides physiological information regarding the endocardium of the heart chamber.

Location and electrical activity is usually measured sequentially on a point-by-point basis at about 50 to 200 points on the internal surface of the heart to construct an electroanatomical depiction of the heart. The generated map may then serve as the basis for deciding on a therapeutic course of action, for example, tissue ablation, to alter the propagation of the heart's electrical activity and to restore normal heart rhythm. Various types of three-dimensional electroanatomical maps are known in the art. These include voltage maps, activation maps, and fractionation maps.

Typically, to generate these maps, the catheter is manually manipulated in the heart chamber by a clinician, such as a doctor. However, due to the movement of the heart during the cardiac mapping or other unwanted movement of the clinician, the manual manipulation of the catheter can be difficult and/or inaccurately administered. Thus, there is an ongoing need to provide additional mapping techniques to improve the cardiac mapping of the heart chamber.

SUMMARY

This disclosure provides design, material, method, system and use alternatives for medical devices.

An example system for autonomous cardiac mapping of a heart chamber includes a processor being configured to acquire a representative geometric shell of the heart chamber, control a robotic device to autonomously navigate a mapping probe to a plurality of locations within the heart chamber based at least in part on the representative geometric shell, and generate a three-dimensional electroanatomical map of the heart chamber based on electrical data collected by the probe at the plurality of locations.

Alternatively or additionally to any of the examples above, the representative geometric shell comprises a template defining a generic geometry of the heart chamber.

Alternatively or additionally to any of the examples above, the representative geometric shell includes image information associated with the heart chamber based on at least one of: computerized tomography scan information, magnetic resonance imaging information, and ultrasound wave information.

Alternatively or additionally to any of the examples above, the processor is further configured to utilize a machine learning process to generate the electroanatomical map of the heart chamber while the autonomous navigation of the mapping probe is performed in the heart chamber.

Alternatively or additionally to any of the examples above, the robotic device autonomously navigates the mapping probe within the heart chamber in real time based on the machine learning process independent of the representative geometric shell.

Alternatively or additionally to any of the examples above, the machine learning process uses data representative of at least one of: a mechanical feedback signal associated with the robotic device, an electrogram signal associated with the heart chamber, an impedance value associated with the heart chamber, a position tracking signal associated with the mapping probe, and the image information associated with the heart chamber.

Alternatively or additionally to any of the examples above, the processor is further configured to detect at least a portion of an inner cardiac wall of the heart chamber using a distance sensor associated with the mapping probe.

Alternatively or additionally to any of the examples above, the distance sensor is an ultrasound transducer configured to measure a distance between the portion of the inner cardiac wall of the heart chamber and the ultrasound transducer.

Alternatively or additionally to any of the examples above, the processor is further configured to guide the mapping probe using the distance sensor to generate the electroanatomical map of the heart chamber.

Alternatively or additionally to any of the examples above, the processor is further configured to relate the electroanatomical map of the heart chamber to three-dimensional positional data corresponding to the plurality of anatomical locations of the heart chamber.

Alternatively or additionally to any of the examples above, the processor is further configured to store, in memory, the electroanatomical map of the heart chamber corresponding to the plurality of anatomical locations of the heart chamber.

Alternatively or additionally to any of the examples above, the processor is further configured to selectively display a region associated with the electroanatomical map of the heart chamber.

Alternatively or additionally to any of the examples above, the system further includes a mechanical interface operatively coupled to the processor and the mapping probe having one or more electrodes coupled to a distal side of the mapping probe.

Alternatively or additionally to any of the examples above, the one or more electrodes is configured to sense electrical signals at the plurality of anatomical locations within the heart chamber.

Alternatively or additionally to any of the examples above, the system further includes a display device coupled to the processor and configured to display a three-dimensional graphical representation of the electroanatomical map of the heart chamber on the display device.

An example method for performing autonomous cardiac mapping of a heart chamber includes acquiring a representative geometric shell of the heart chamber, controlling a robotic device to autonomously navigate a mapping probe to a plurality of locations within the heart chamber based at least in part on the representative geometric shell, and generating a three-dimensional electroanatomical map of the heart chamber based on electrical data collected by the probe at the plurality of locations.

Alternatively or additionally to any of the examples above, the representative geometric shell comprises a template defining a generic geometry of the heart chamber.

Alternatively or additionally to any of the examples above, the representative geometric shell includes image information associated with the heart chamber based on at least one of: computerized tomography scan information, magnetic resonance imaging information, and ultrasound wave information.

Alternatively or additionally to any of the examples above, generating the electroanatomical map of the heart chamber comprises utilizing a machine learning process to generate the electroanatomical map of the heart chamber while the autonomous navigation of the mapping probe is performed in the heart chamber.

Alternatively or additionally to any of the examples above, autonomously navigating the mapping probe within the heart chamber in real time based on the machine learning process independent of the representative geometric shell.

Alternatively or additionally to any of the examples above, the machine learning process uses data representative of at least one of: a mechanical feedback signal associated with the robotic device, an electrogram signal associated with the heart chamber, an impedance value associated with the heart chamber, a position tracking signal associated with the mapping probe, and the image information associated with the heart chamber.

Alternatively or additionally to any of the examples above, generating the electroanatomical map comprises detecting at least a portion of an inner cardiac wall of the heart chamber using a distance sensor associated with the mapping probe.

Alternatively or additionally to any of the examples above, utilizing an ultrasound transducer as the distance sensor to measure a distance between the portion of the inner cardiac wall of the heart chamber and the ultrasound transducer, and guiding the mapping probe using the distance sensor associated with the mapping probe to generate the electroanatomical map of the heart chamber.

Alternatively or additionally to any of the examples above, generating the electroanatomical map comprises relating the electroanatomical map of the heart chamber to three-dimensional positional data corresponding to the plurality of anatomical locations of the heart chamber.

Alternatively or additionally to any of the examples above, storing, in memory, the electroanatomical map of the heart chamber corresponding to the plurality of anatomical locations of the heart chamber.

Alternatively or additionally to any of the examples above, selectively displaying a region associated with the electroanatomical map of the heart chamber.

Alternatively or additionally to any of the examples above, using a mechanical interface operatively coupled to the processor and the mapping probe having one or more electrodes coupled to a distal side of the mapping probe.

An another system for autonomous cardiac mapping of a heart chamber includes a processor being configured to acquire a representative geometric shell of the heart chamber, control a robotic device to autonomously navigate a mapping probe to a plurality of locations within the heart chamber based at least in part on the representative geometric shell, and generate a three-dimensional electroanatomical map of the heart chamber based on electrical data collected by the probe at the plurality of locations.

Alternatively or additionally to any of the examples above, the representative geometric shell comprises a template defining a generic geometry of the heart chamber.

Alternatively or additionally to any of the examples above, the representative geometric shell includes image information associated with the heart chamber based on at least one of: computerized tomography scan information, magnetic resonance imaging information, and ultrasound wave information.

Alternatively or additionally to any of the examples above, the processor is further configured to utilize a machine learning process to generate the electroanatomical map of the heart chamber while the autonomous navigation of the mapping probe is performed in the heart chamber.

Alternatively or additionally to any of the examples above, the processor is further configured to autonomously navigate the mapping probe within the heart chamber in real time based on the machine learning process independent of the representative geometric shell, and the machine learning process uses data representative of at least one of: a mechanical feedback signal associated with the robotic device, an electrogram signal associated with the heart chamber, an impedance value associated with the heart chamber, a position tracking signal associated with the mapping probe, and the image information associated with the heart chamber.

Alternatively or additionally to any of the examples above, the processor is further configured to detect at least a portion of an inner cardiac wall of the heart chamber using a distance sensor associated with the mapping probe, and an ultrasound transducer is used as the distance sensor to measure a distance between the portion of the inner cardiac wall of the heart chamber and the ultrasound transducer.

Alternatively or additionally to any of the examples above, the system further includes a mechanical interface operatively coupled to the processor and the mapping probe having one or more electrodes coupled to a distal side of the mapping probe.

Example one or more computer-readable media having embodied thereon computer-executable instructions that, when executed by a processor, are configured to cause the processor to instantiate one or more program components. The one or more program components include a processing system being configured to acquire a representative geometric shell of a heart chamber, control a robotic device to autonomously navigate a mapping probe to a plurality of locations within the heart chamber based at least in part on the representative geometric shell, and generate a three-dimensional electroanatomical map of the heart chamber based on electrical data collected by the probe at the plurality of locations.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The disclosure may be more completely understood in consideration of the following detailed description in connection with the accompanying drawings, in which.

Figure 1:
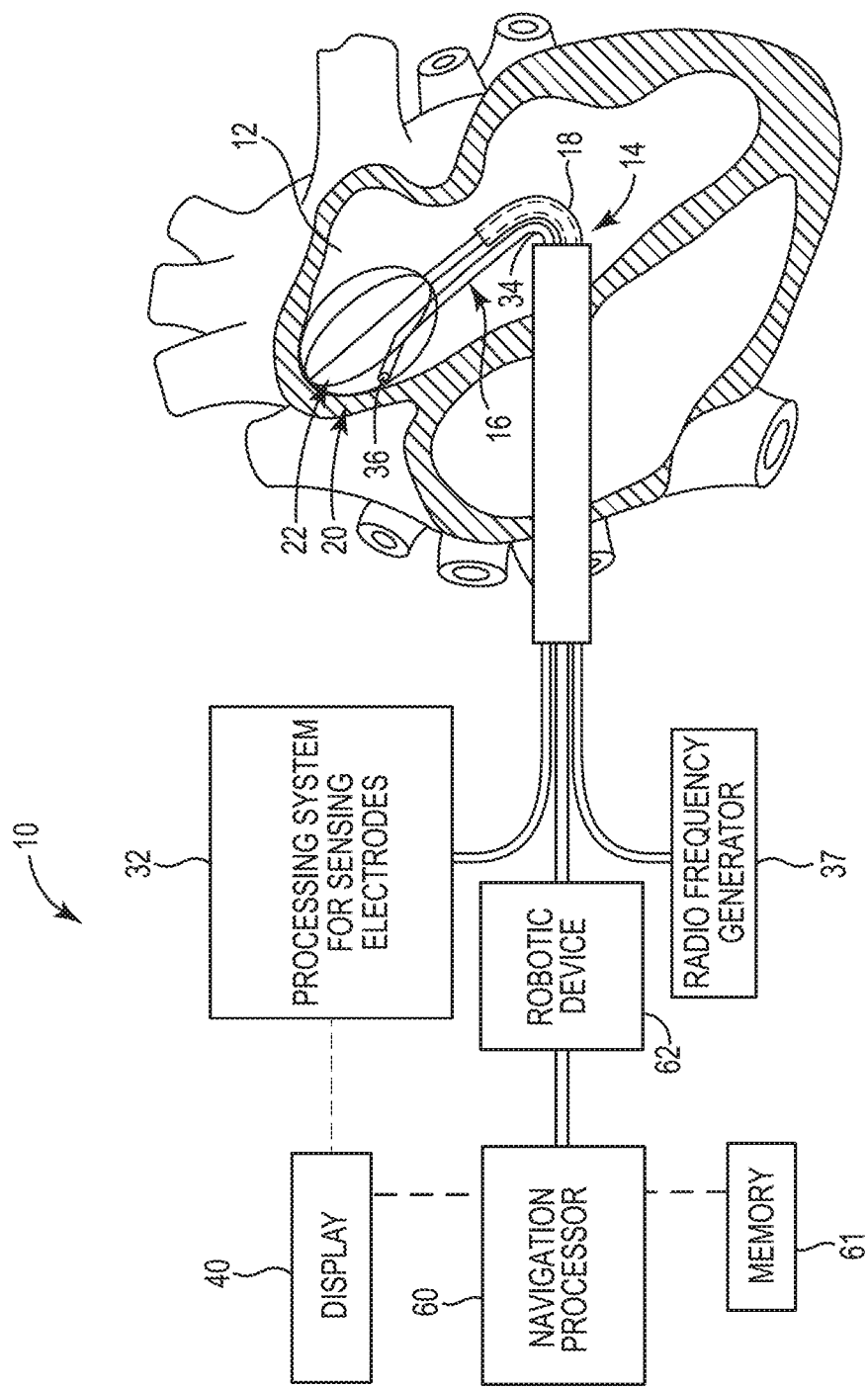
FIG. 1 is a schematic block diagram depicting an illustrative navigation system in accordance with embodiments of the disclosed subject matter.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an example", "some examples", "other examples", etc., indicate that the example described may include one or more particular features, structures, and/or characteristics. However, such recitations do not necessarily mean that all examples include the particular features, structures, and/or characteristics. Additionally, when particular features, structures, and/or characteristics are described in connection with one example, it should be understood that such features, structures, and/or characteristics may also be used in connection with other examples whether or not explicitly described unless clearly stated to the contrary. Also, when particular features, structures, and/or characteristics are described in connection with one example, it is implicit that other examples may include less than all of the disclosed features, structures, and/or characteristics in all combinations.

The following detailed description should be read with reference to the drawings in which similar elements in different drawings are numbered the same. The drawings, which are not necessarily to scale, depict illustrative embodiments and are not intended to limit the scope of the disclosure.

Mapping the electrophysiology of heart rhythm disorders often involves the introduction of a basket catheter (e.g. the ORION™ catheter marketed by Boston Scientific Corporation) or other mapping/sensing device having a plurality of sensors into a cardiac chamber. The sensors, e.g., electrodes, detect physiological signals, such as cardiac electrical activity, at sensor locations. It may be desirable to have detected cardiac electrical activity processed into electrogram (EGM) signals that accurately represent cellular excitation through cardiac tissue relative to the sensor locations. A processing system may then analyze and output the signal to a display device. Further, the processing system may output the signal as processed output, such as a static or dynamic activation map. A user, such as a physician, may use the processed output to perform a diagnostic procedure.

FIG. 1 is a schematic view of a system 10 for accessing a targeted tissue region in the body for diagnostic and/or therapeutic purposes. FIG. 1 generally shows the system 10 deployed in the left atrium of the heart. Alternatively, system 10 can be deployed in other regions of the heart, such as the left ventricle, right atrium, or right ventricle.

The system 10 includes a mapping catheter or probe 14 and an ablation catheter or probe 16. Each probe 14/16 may be separately introduced into the selected heart region of a heart chamber 12 through a vein or artery (e.g., the femoral vein or artery) using a suitable percutaneous access technique. Alternatively, the mapping probe 14 and the ablation probe 16 can be assembled in an integrated structure for simultaneous introduction and deployment in the heart region of the heart chamber 12.

The mapping probe 14 generally includes a flexible catheter body 18 carrying, at its distal end, a three-dimensional multiple electrode structure 20. In the illustrated embodiment, the structure 20 takes the form of a basket defining an open interior space 22 (see FIG. 2), although other multiple electrode structures could be used. The structure 20 carries a plurality of mapping electrodes 24 (not explicitly shown on FIG. 1, but shown on FIG. 2) each having an electrode location on the structure 20. Each electrode 24 may be configured to sense or detect intrinsic physiological activity, for example represented as electrical signals, in an anatomical region adjacent to each electrode 24.

In addition, the electrodes 24 may be configured to detect activation signals of the intrinsic physiological activity within the anatomical structure. For example, intrinsic cardiac electrical activity may include repeating or semi-repeating waves of electrical activity with relatively large spikes in activity at the beginning of activation events. The electrodes 24 may sense such activation events and the times at which such activation events occur. Generally, the electrodes 24 may sense activation events at different times as an electrical activity wave propagates through the heart. For instance, an electrical wave may begin near a first group of electrodes 24, which may sense an activation event at relatively the same time or within a relatively small window of time. As the electrical wave propagates through the heart, a second group of electrodes 24 may sense the activation event of the electrical wave at times later than the first group of electrodes 24.

The electrodes 24 are electrically coupled to a processing system 32. A signal wire (not shown) may be electrically coupled to each electrode 24 on structure 20. The signal wires may extend through the body 18 of the probe 14 and electrically couple each electrode 24 to an input of the processing system 32. The electrodes 24 sense cardiac electrical activity in the anatomical region, e.g., myocardial tissue, adjacent to their physical location within the heart. The sensed cardiac electrical activity (e.g., electrical signals generated by the heart which may include activation signals) may be processed by the processing system 32 to assist a user, for example a physician, by generating processed output—e.g. an electroanatomical map (e.g., a vector field map, an activation time map) or a Hilbert transform diagram—to identify one or more sites within the heart appropriate for a diagnostic and/or treatment procedure, such as an ablation procedure.

For example, the processing system 32 may identify a near-field signal component (e.g., activation signals originating from cellular tissue adjacent to the mapping electrodes 24) or an obstructive far-field signal component (e.g., activation signals originating from non-adjacent tissue). In such examples where the structure 20 is disposed in an atrium of the heart, as in FIG. 1, the near-field signal component may include activation signals originating from atrial myocardial tissue whereas the far-field signal component may include activation signals originating from ventricular myocardial tissue. The near-field activation signal component may be further analyzed to find the presence of a pathology and to determine a location suitable for ablation for treatment of the pathology (e.g., ablation therapy).

The processing system 32 may include dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired physiological activity. In some examples, the processing system 32 includes a general purpose microprocessor and/or a specialized microprocessor (e.g., a digital signal processor, or DSP, which may be optimized for processing activation signals) that executes instructions to receive, analyze and display information associated with the received physiological activity. In such examples, the processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that processing system 32 can take any suitable form for receiving electrical signals and processing the received electrical signals.

In addition, the processing system 32 may be configured to measure the sensed cardiac electrical activity in the myocardial tissue adjacent to the electrodes 24. For example, the processing system 32 may be configured to detect cardiac electrical activity associated with a dominant rotor or divergent activation pattern in the anatomical feature being mapped. Dominant rotors and/or divergent activation patterns may have a role in the initiation and maintenance of atrial fibrillation, and ablation of the rotor path, rotor core, and/or divergent foci may be effective in terminating the atrial fibrillation. The processing system 32 processes the sensed cardiac electrical activity to generate a display of relevant characteristics. Such processed output may include isochronal maps, activation time maps, phase maps, action potential duration (APD) maps, Hilbert transform diagrams, vector field maps, contour maps, reliability maps, electrograms, cardiac action potentials and the like. The relevant characteristics may assist a user to identify a site suitable for ablation therapy.

The ablation probe 16 includes a flexible catheter body 34 that carries one or more ablation electrodes 36. The one or more ablation electrodes 36 are electrically connected to a radio frequency (RF) generator 37 that is configured to deliver ablation energy to the one or more ablation electrodes 36. The ablation probe 16 may be movable with respect to the anatomical feature to be treated, as well as the structure 20 of the mapping probe 14. The ablation probe 16 may be positionable between or adjacent to the electrodes 24 of the structure 20 as the one or more ablation electrodes 36 are positioned with respect to the tissue to be treated.

The processing system 32 may output data to a suitable device, for example, a display device 40, which may display relevant information for a user. In some examples, the device 40 is a CRT, LED, or other type of display, or a printer. The device 40 presents the relevant characteristics in a format useful to the user.

In addition, the mapping probe 14 is operatively coupled to a navigation processor 60 that is configured to track the position of the structure 20 and its components within a pre-determined space, and to generate position-identifying output for display on the device 40 that aids the user in guiding the mapping probe 14 and/or the ablation electrode(s) 36 into contact with tissue at the site identified for ablation.

It is emphasized that in some embodiments the system 10 does not include the ablation probe 16. That is, the mapping probe 14 and associated hardware and software (e.g., the processing system 32 and the display 40) can be utilized as a stand-alone electroanatomical mapping system independent of the ablation probe 16 and corresponding hardware and software. In one particular embodiment, the mapping probe 14, the processing system 32, the display 40 and the navigation processor 60 are components of the RHYTHMIA™ mapping system marketed by Boston Scientific Corporation.

In the illustrated embodiment, the mapping probe 14 and/or the ablation probe 16 is operatively coupled to a robotic device 62 to aid the user in manipulating the mapping probe 14 and/or the ablation probe 16. In embodiments, the robotic device 62 is configured to control movement of the mapping probe 14 and/or the ablation probe 16 within the heart chamber 12. For example, the robotic device 62 is attached to the mapping probe 14 in mechanical relationship to navigate the structure 20 of the mapping probe 14 within the heart chamber 12. Also, the robotic device 62 is communicably coupled to the processing system 32 and/or the navigation processor 60 to provide mechanical feedback information associated with the robotic device 62. One particular example of the robotic device 62 is described below in paragraphs relating to FIG. 4.

Figure 2:
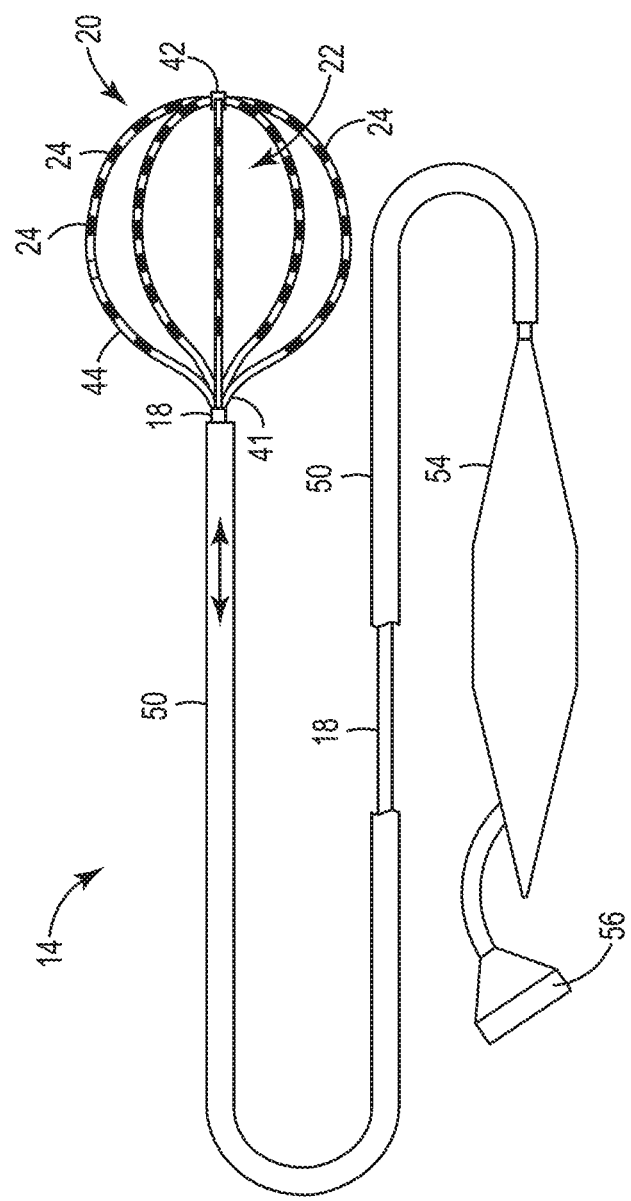
FIG. 2 is a schematic diagram depicting an exemplary mapping catheter in accordance with embodiments of the disclosed subject matter.

FIG. 2 illustrates the mapping catheter 14 and shows the electrodes 24 at the distal end suitable for use in the system 10 shown in FIG. 1. As shown, the illustrated three-dimensional multiple electrode structure 20 includes a base member 41 and an end portion 42 between which flexible splines 44 generally extend in a circumferentially spaced relationship. As discussed herein, the structure 20 may take the form of a basket defining an open interior space 22. In some examples, the splines 44 are made of a resilient inert material, such as Nitinol, other metals, silicone rubber, suitable polymers, or the like and are connected between the base member 41 and the end portion 42 in a resilient, pretensioned condition, to bend and conform to the tissue surface they contact. In the example illustrated in FIG. 2, eight splines 44 form the three-dimensional multiple electrode structure 20. Additional or fewer splines 44 could be used in other examples. As illustrated, each spline 44 carries eight mapping electrodes 24. Additional or fewer mapping electrodes 24 could be disposed on each spline 44 in other examples of three-dimensional multiple electrode structure 20. In the example illustrated in FIG. 2, the structure 20 is relatively small (e.g., 40 mm or less in diameter). In alternative examples, the structure 20 is even smaller or larger (e.g., less than or greater than 40 mm in diameter).

A slidable sheath 50 may be movable along the major axis of catheter body 18. Moving the sheath 50 distally relative to the catheter body 18 may cause the sheath 50 to move over the structure 20, thereby collapsing structure 20 into a compact, low profile condition suitable for introduction into and/or removal from an interior space of an anatomical structure, such as, for example, the heart. In contrast, moving the sheath 50 proximally relative to the catheter body may expose the structure 20, allowing the structure 20 to elastically expand and assume the pretensioned position illustrated in FIG. 2. Alternatively, in some embodiments, the structure 20 may be extendable and retractable relative to the sheath 50 (by means of a control mechanism operable by a user). In such embodiments, the structure 20 is withdrawn within the sheath 50 and thereby maintained in a collapsed configuration during advancement of the structure 20 through the patient's vasculature to the target cardiac region (e.g., the left atrium) and then extended from the sheath 50 so as to allow the structure 20 to assume its expanded configuration.

The signal wires (not shown) electrically coupled to the respective mapping electrodes 24 may extend through the body 18 of the mapping probe 14 (or otherwise through and/or along body 18) into a handle 54, in which they are coupled to an external connector 56, which may be a multiple pin connector. The connector 56 electrically couples the mapping electrodes 24 to the processing system 32. The mapping probe 14 is mechanically coupled to the robotic device 62. It should be understood that these descriptions are just examples.

In some embodiments, the mapping probe 14 may also include one or more navigation sensors (not shown) that provide an output to the navigation processor 60 (see FIG. 1) as part of a three-dimensional navigation system incorporated into the system 10. The navigation sensor, when present, can be comprised of any navigation sensor known in the art or later developed. In one embodiment, the navigation sensor may comprise a magnetic field sensor, whether now known or later developed, that generates an output in response to a three-dimensional electromagnetic field generated by one or more external field generators. In particular, the navigation sensor(s) may include sensors such as inductive sensing coils and/or various sensing elements such as magneto-resistive (MR) sensing elements (e.g., anisotropic magneto-resistive (AMR) sensing elements, giant magneto-resistive (GMR) sensing elements, tunneling magneto-resistive (TMR) sensing elements, Hall effect sensing elements, colossal magneto-resistive (CMR) sensing elements, extraordinary magneto-resistive (EMR) sensing elements, spin Hall sensing elements, and the like), giant magneto-impedance (GMI) sensing elements, and/or fluxgate sensing elements.

Some additional details regarding these and other example mapping systems and methods for processing signals generated by a mapping catheter can be found in U.S. Pat. Nos. 6,070,094, 6,233,491, and 6,735,465, the disclosures of which are hereby expressly incorporated herein by reference.

One particular example of the mapping probe 14 is the ORION™ high resolution mapping catheter marketed by Boston Scientific Corporation.

Figure 3:
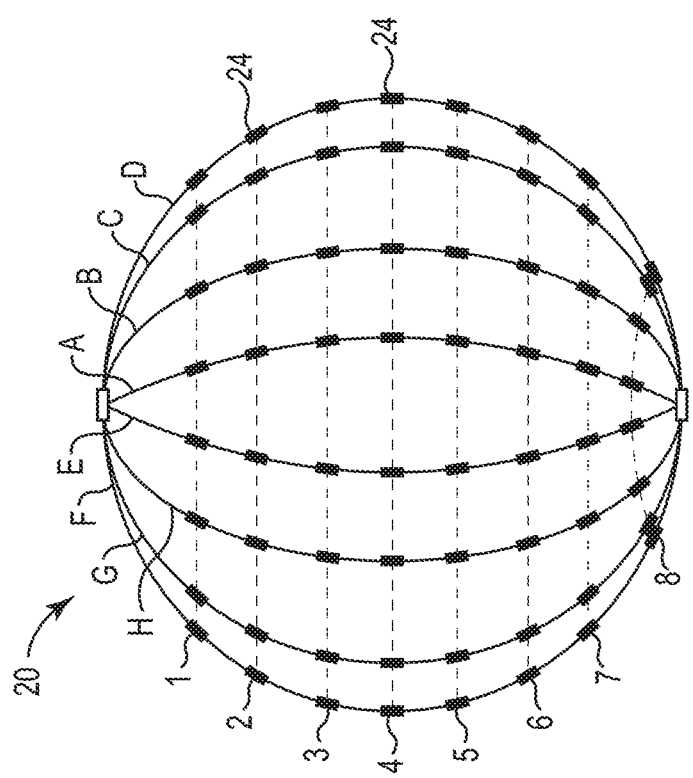
FIG. 3 is a schematic diagram depicting an exemplary electrode structure of the mapping catheter shown in FIG. 2 in accordance with embodiments of the disclosed subject matter.

To illustrate the operation of the system 10, FIG. 3 is a schematic side view of an example of the basket structure 20 including the plurality of mapping electrodes 24. In the illustrated example, the basket structure 20 includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While the arrangement of sixty-four mapping electrodes 24 is shown disposed on the basket structure 20, the mapping electrodes 24 may alternatively be arranged in different numbers (more or fewer splines and/or electrodes), on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g. left atrium, left ventricle, right atrium, or right ventricle of the heart), the processing system 32 may be configured to record the cardiac electrical activity from each electrode 24. Further, the recorded cardiac electrical activity may be related to the physiological activity of the adjacent anatomical structure. For instance, cardiac electrical activity sensed by the electrodes 24 may include activation signals which may indicate an onset of physiological activity (e.g. contraction of the heart). Further, cardiac electrical activity corresponding to physiological activity may be sensed in response to intrinsic physiological activity (e.g. intrinsically generated electrical signals) or based on a predetermined pacing protocol instituted by at least one of the plurality of electrodes 24 (e.g. delivered electrical signals delivered by a pacing device).

The electrodes 24 are configured to sense a change in the voltage potential of a propagating cellular activation wavefront. The change in voltage potential of cellular tissue may be sensed, collected and displayed as an electrogram (EGM). An electrogram may be a visual representation of the change in voltage potential of the cellular tissue over time. Additionally, it may be desirable to define a specific characteristic of an electrogram as a "fiducial" point of the electrical signal. For purposes of this disclosure, a fiducial point may be understood as a characteristic of an electrogram that can be utilized as an identifying characteristic of cellular activation. Fiducial points may correspond to the peak magnitude, change in slope, and/or deflection of the electrical signal. It is contemplated that fiducial points may include other characteristics of an electrogram or other signal used to generate diagnostic and/or processed output. Further, fiducial points may be identified manually by a clinician and/or automatically by processing system 32.

Figure 4:
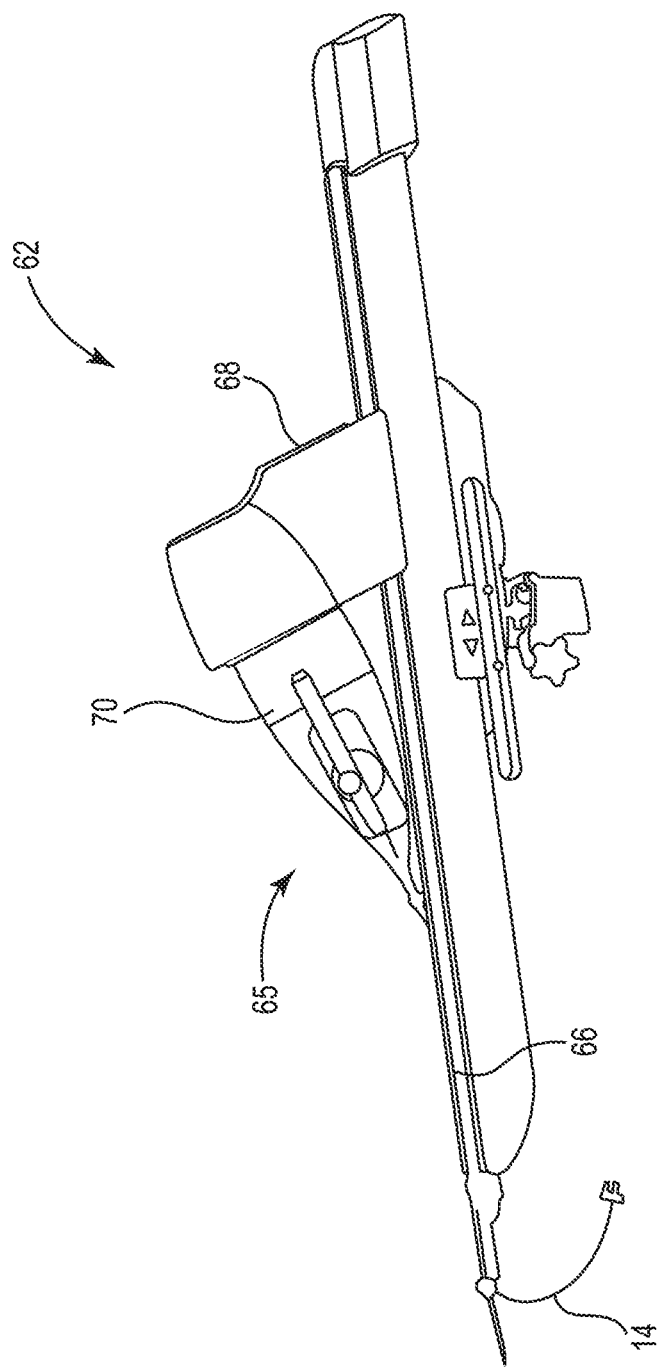
FIG. 4 is a schematic diagram depicting an exemplary robotic device used in the navigation system shown in FIG. 1 in accordance with embodiments of the disclosed subject matter.

FIG. 4 illustrates an exemplary robotic device 62 configured to control the movement of the mapping probe 14 within the heart chamber 12. In the illustrated embodiment, a catheter robotic system is shown to allow for the manipulation of the movement of the mapping probe 14 through the adjustment of the robotic device 62. During operation, the mapping probe 14 can be advanced and withdrawn using a motor-driven unit and can be maneuvered by the user. In various embodiments, the robotic device 62 includes a mechanical interface 65 operatively coupled to the navigation processor 60 and the mapping probe 14 having one or more electrodes 24 coupled to a distal side of the mapping probe 14. The one or more electrodes 24 can sense electrical signals at a plurality of anatomical locations within the heart chamber 12. In one embodiment, the robotic device 62 can be controlled by processing system 32 and the user can interact with a catheter manually after detaching it from the robotic system.

One particular example of the robotic device 62 is the AMIGO™ robotic system marketed by Catheter Precision, Inc.

The inventors of the present disclosure have determined that the robotic device 62 of the system 10 can be utilized to provide the user with autonomous catheter navigation tools for controlling the movement of the mapping probe 14 within the heart chamber 12, and in doing so, assist the user in generating the three-dimensional electroanatomical map of the heart chamber 12. In various embodiments, the robotic device 62 is communicably coupled to the processing system 32 and/or the navigation processor 60 to provide mechanical feedback information associated with the robotic device 62. In one embodiment, a particular example of the robotic system (AMIGO™) can be utilized for autonomous mapping after some modifications.

When the mapping probe 14 is inserted into the heart chamber 12 (e.g., into the left atrium), the mapping probe 14 is manipulated by the robotic device 62. In use, the robotic device 62 autonomously controls the movement of the mapping probe 14 within the heart chamber 12. For example, the robotic device 62 can autonomously advance, withdraw, rotate, and deflect a distal tip of the mapping probe 14 as needed. Included in the robotic device 62 is a track 66 configured to slidably receive the mapping probe 14. For axial or translation movement of the mapping probe 14, a sled member 68 of the robotic device 62 is used to advance or withdraw the mapping probe 14. The deflective or articulation movement of the mapping probe 14 can also be controlled by the sled member 68. For rotational movement of the mapping probe 14, a rotating member 70 of the robotic device 62 is used to rotate the mapping probe 14. Other movements, such as the deployment and/or un-deployment of the basket structure 20 of the mapping probe 14, can be controlled by the robotic device 62. Further, the robotic device 62 can also deploy a catheter in addition to providing advancement, withdrawal, articulation and rotation movement.

Figure 5:
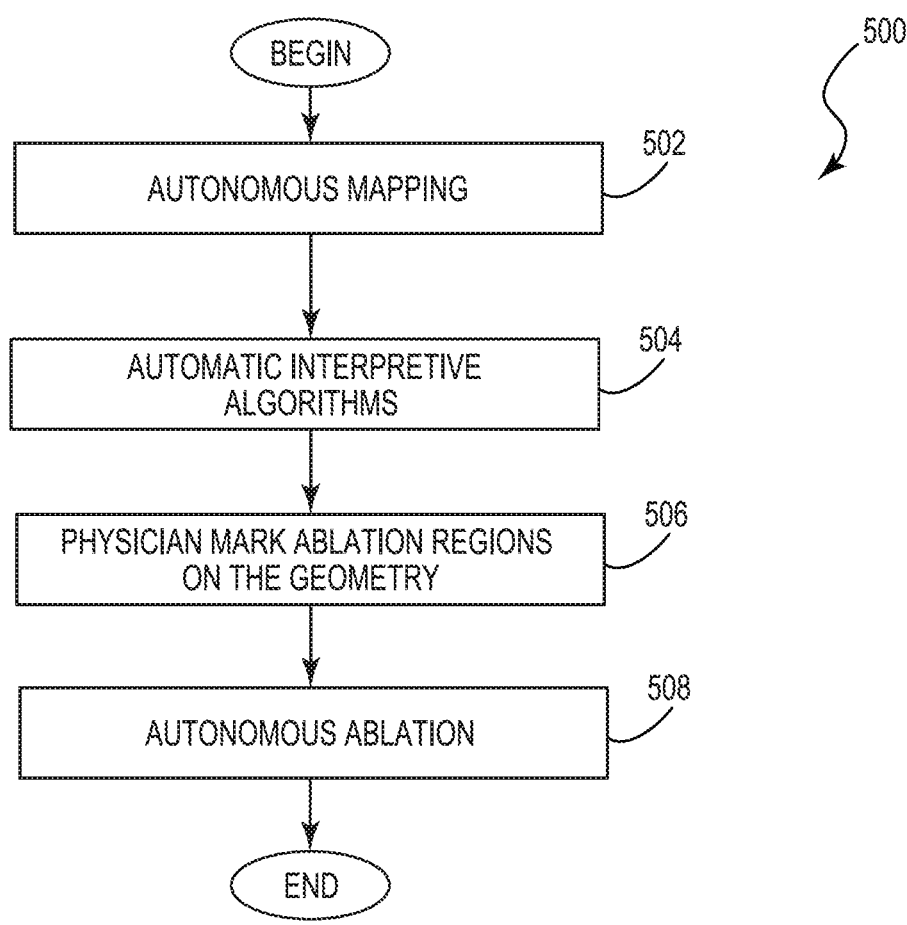
FIG. 5 is a flow diagram depicting an illustrative method of an exemplary process of autonomous mapping and ablation procedures using the navigation system of FIG. 1 in accordance with embodiments of the disclosed subject matter.

FIG. 5 is a flow diagram showing an exemplary method of autonomous mapping and ablation procedures using the navigation system 10. As disclosed herein, the system 10 is not particularly limited and can perform any of the methods described within the scope of this disclosure. In FIG. 5, a method 500 of performing the autonomous mapping and ablation procedures is shown using the system 10.

At block 502, the autonomous mapping procedure is performed by the system 10 having various components, such as the robotic device 62, the mapping probe 14, the processing system 32, the display 40 and the navigation processor 60. For example, the user, such as a doctor, can initiate the mapping procedure by inputting a request to generate a partial or complete electroanatomical map of the heart chamber 12 using an input device, such as a keyboard or interactive screen, operatively coupled to the system 10. Then, the robotic device 62 autonomously generates the partial or complete three-dimensional electroanatomical map of the heart chamber 12 based on electrical data collected by the mapping probe 14.

At block 504, the system 10 automatically identifies one or more regions of the heart chamber 12 and interprets the generated electroanatomical map for performing a substrate analysis of the heart chamber 12. For example, an automatic interpretive algorithm can be used to perform the substrate analysis. One particular example of the interpretive algorithm is the LUMIPOINT™ computer software marketed by Boston Scientific Corporation.

At block 506, the user (e.g., a physician) can mark or target one or more ablation regions on the geometry of the endocardium surface within the heart chamber 12 based on the substrate analysis performed by the interpretive algorithm. In another embodiment, identifying and marking the ablation regions can be performed autonomously by the system 10 without manual intervention of the user.

At block 508, the system 10 automatically switches control to the ablation probe 16 and autonomously performs the ablation procedure by navigating the ablation probe 16 to the marked (or targeted) ablation regions. For example, the system 10 can utilize lesion indexing, direct sensing, or force techniques to perform the ablation procedure. Thus, it is advantageous that the system 10 provides various autonomous methods to perform multiple procedures without user intervention.

Figure 6:
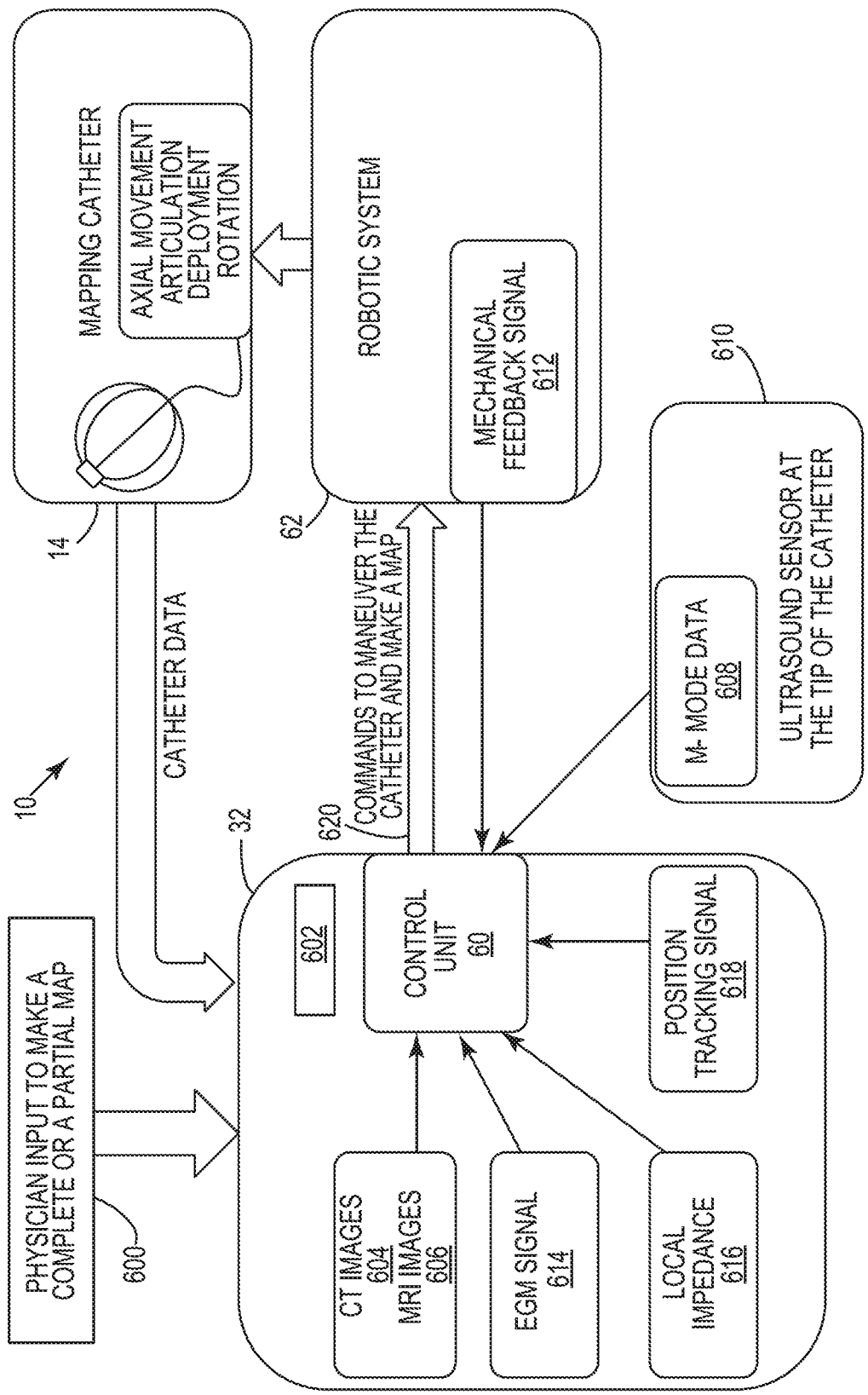
FIG. 6 is a schematic diagram depicting an exemplary autonomous mapping procedure shown in FIG. 5 in accordance with embodiments of the disclosed subject matter.

FIG. 6 illustrates a schematic diagram of an exemplary autonomous mapping procedure performed by the system 10 as described at block 502 of FIG. 5. In FIG. 6, the system 10 configured to perform the autonomous cardiac mapping of the heart chamber 12 is shown. In this example, the user, such as a doctor, initially inserts the mapping probe 14 into the heart chamber 12 (e.g., the left atrium) and initiates the mapping procedure by inputting a request (or demand) 600 to generate a partial or complete three-dimensional electroanatomical map of the heart chamber 12. In another example, the request 600 can be automatically received by the processing system 32 from another control unit associated with the system 10.

When the processing system 32 receives the request 600, a control unit, such as the navigation processor 60, automatically acquires a representative geometric shell 602 of the heart chamber 12 to initially begin the mapping procedure based on the representative geometric shell 602. At the beginning of the mapping procedure, the representative geometric shell 602 is used to initially guide the mapping probe 14 within the heart chamber 12. In one embodiment, the representative geometric shell 602 can be registered in a three-dimensional image coordinate system of the system 10 to be served as an initial reference between heart image and physical coordinate systems.

In embodiments, the representative geometric shell 602 includes a template defining a generic geometry of the heart chamber 12 of a human (e.g., based on existing or archived data of a selected number of patients). Although the template may not be patient-specific, in certain cases, the template can define a specific geometry of the heart chamber 12 of a specific patient. For example, the template includes information representative of the geometry for at least a portion of the heart chamber 12 where the distal tip of the mapping probe 14 is positioned. In another example, the template includes information representative of the full geometry of the heart chamber 12.

In various embodiments, the representative geometric shell 602 includes image information associated with the heart chamber 12 based on at least one of: computerized tomography (CT) scan information 604, magnetic resonance imaging (MRI) information 606, and ultrasound wave information 608. In one example, the CT scan information 604 can be provided by a CT scanning system, and the MRI information 606 can be provided by an MRI scanning system. In another example, the ultrasound wave information 608 can include M-mode data generated by an ultrasound sensor 610 disposed at the distal tip of the mapping probe 14. For example, the M-mode data can be collected by the ultrasound sensor 601 in real time during the mapping procedure.

The navigation processor 60 is configured to control the robotic device 62 to autonomously navigate the mapping probe 14 to a plurality of locations within the heart chamber 12 based at least in part on the representative geometric shell 602. During operation, the navigation processor 60 utilizes a machine learning process or algorithm to generate the electroanatomical map of the heart chamber 12 while the autonomous navigation of the mapping probe 14 is performed in the heart chamber 12. The electroanatomical map of the heart chamber 12 can be generated based on electrical data collected by the mapping probe 14 at the plurality of locations. In one embodiment, the geometry of the heart chamber 12 can also be updated by the navigation processor 60 in real time based on the collected data.

Typically, when the representative geometric shell 602 includes partial geometry information for only a portion of the heart chamber 12, the navigation processor 60 can perform the mapping procedure only for that portion of the heart chamber 12 because the geometry information for the rest of the heart chamber 12 is not available. However, it is advantageous that in the system 10, the navigation processor 60 is configured to continuously control the robotic device 62 beyond the portion of the heart chamber 12. Specifically, the robotic device 62 can autonomously navigate the mapping probe 14 within the heart chamber 12 for the rest of the heart chamber 12 in real time based on the machine learning process independent of (or without using) the representative geometric shell 602.

Thus, the machine learning process provides an improved continuous mapping procedure for the system 10. In embodiments, the machine learning process uses data representative of at least one of: a mechanical feedback signal 612 associated with the robotic device 62, an electrogram signal 614 associated with the heart chamber 12, a local impedance value 616 associated with the heart chamber 12, a position tracking signal 618 associated with the mapping probe 14, and the image information associated with the heart chamber 12. In one embodiment, the image information can be used to navigate the mapping probe 14. In another embodiment, the mechanical feedback signal 612, the electrogram signal 614, and the local impedance value 616 can be used for a contact-sensing function (e.g., for detecting an internal wall within the heart chamber 12).

For example, the mechanical feedback signal 612 can include the mechanical feedback information associated with the robotic device 62 (e.g., displacement or articulation movement of the sled member 68 or the rotating member 70). In another example, the electrogram signal 614 can include the electrical data detected by the mapping probe 14 at the plurality of locations within the heart chamber 12. Also, the local impedance value 616 can include cardiac local impedance indicative of cardiac local wall motion or movement within the heart chamber 12. Further, the position tracking signal 618 can include positional information of the mapping probe 14 (e.g., catheter data relating to axial movement, articulation, deployment, or rotation of the mapping probe 14).

As such, it is advantageous that during the machine learning process, the navigation processor 60 automatically learns a profile or configuration of the endocardium surface of the heart chamber 12. In various embodiments, the navigation processor 60 transmits one or more computer-executable commands 620 to the robotic device 62 to autonomously and continuously generate the electroanatomical map for the rest of the heart chamber 12 without relying on the representative geometric shell 602.

In certain embodiments, the navigation processor 60 can update the electroanatomical map in real time using the information, such as the feedback signal 612, the electrogram signal 614, the local impedance value 616, and the position tracking signal 618, associated with the heart chamber 12 as the electroanatomical map is being generated. Also, in real time, the navigation processor 60 can correct or adjust physiological mapping data associated with the electroanatomical map of the heart chamber 12 while the autonomous navigation of the mapping probe is being performed. Similarly, during the machine learning process, the navigation processor 60 can update or correct the representative geometric shell 602 as desired for the subsequent use of the specific patient.

Figure 7:
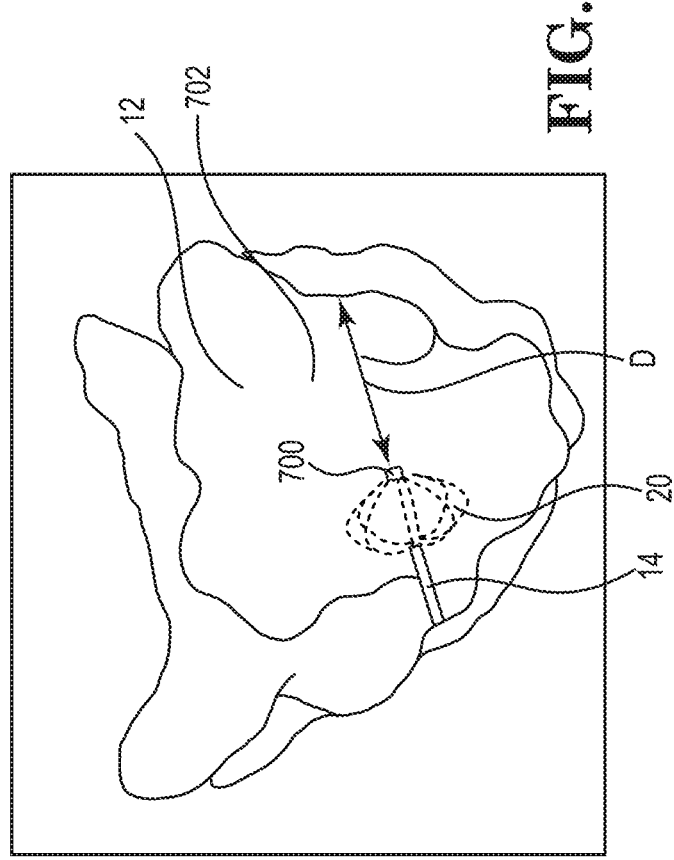
FIGS. 7 and 8 illustrate an exemplary distance sensor used by the navigation system shown in FIG. 1 in accordance with embodiments of the disclosed subject matter.
Figure 8:
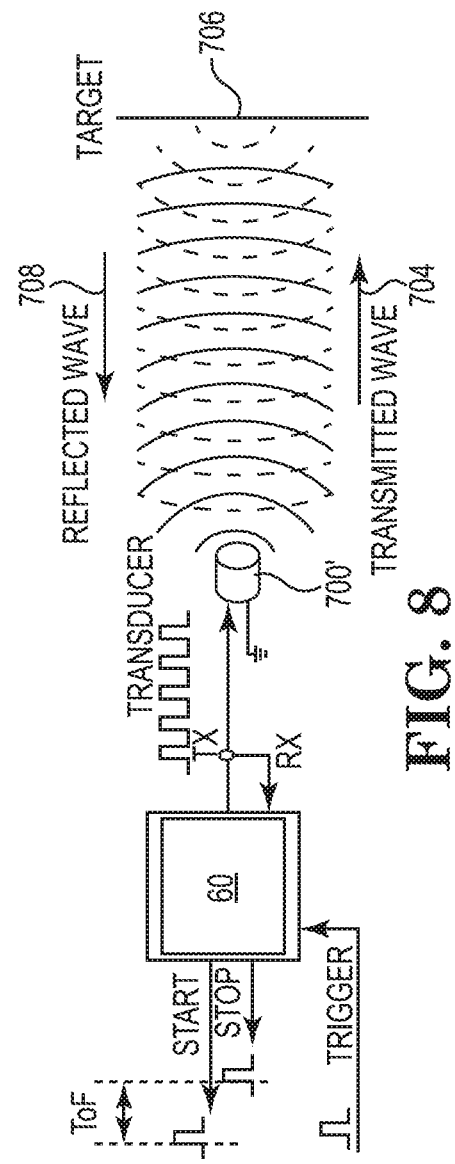

FIGS. 7 and 8 illustrate an exemplary distance sensor 700 that can be used during the mapping procedure performed by the system 10. In FIG. 7, to enhance the contact-sensing function, the distance sensor 700 is disposed at the distal tip of the mapping probe 14 and is used to detect at least a portion of an inner cardiac wall 702 of the heart chamber 12. In one embodiment, as shown in FIG. 8, the distance sensor 700 can be an ultrasound transducer 700' configured to measure a distance D (FIG. 7) between the portion of the inner cardiac wall 702 of the heart chamber 12 and the ultrasound transducer 700'. As such, it is advantageous that the navigation processor 60 can guide the mapping probe 14 using the distance sensor 700 to generate the electroanatomical map of the heart chamber 12 without touching the inner cardiac wall 702 of the heart chamber 12, thereby alleviating the risk of perforating the wall 702.

For example, as shown in FIG. 8, the transducer 700' transmits an ultrasound wave 704 toward a target site 706 of the inner cardiac wall 702 of the heart chamber 12, and receives a reflected wave 708 from the target site 706. The navigation processor 60 can determine the distance D between the target site 706 and the transducer 700' based on a comparison between the transmitted wave 704 and the reflected wave 708 (e.g., a time difference). In another embodiment, to enhance the contact-sensing function (e.g., for additional contact feedback), a force sensor (not shown) can be disposed between the electrode structure 20 and the catheter body 18 of the mapping probe 14. For example, the force sensor can be a resilient biasing member, such as a spring.

Figure 9:
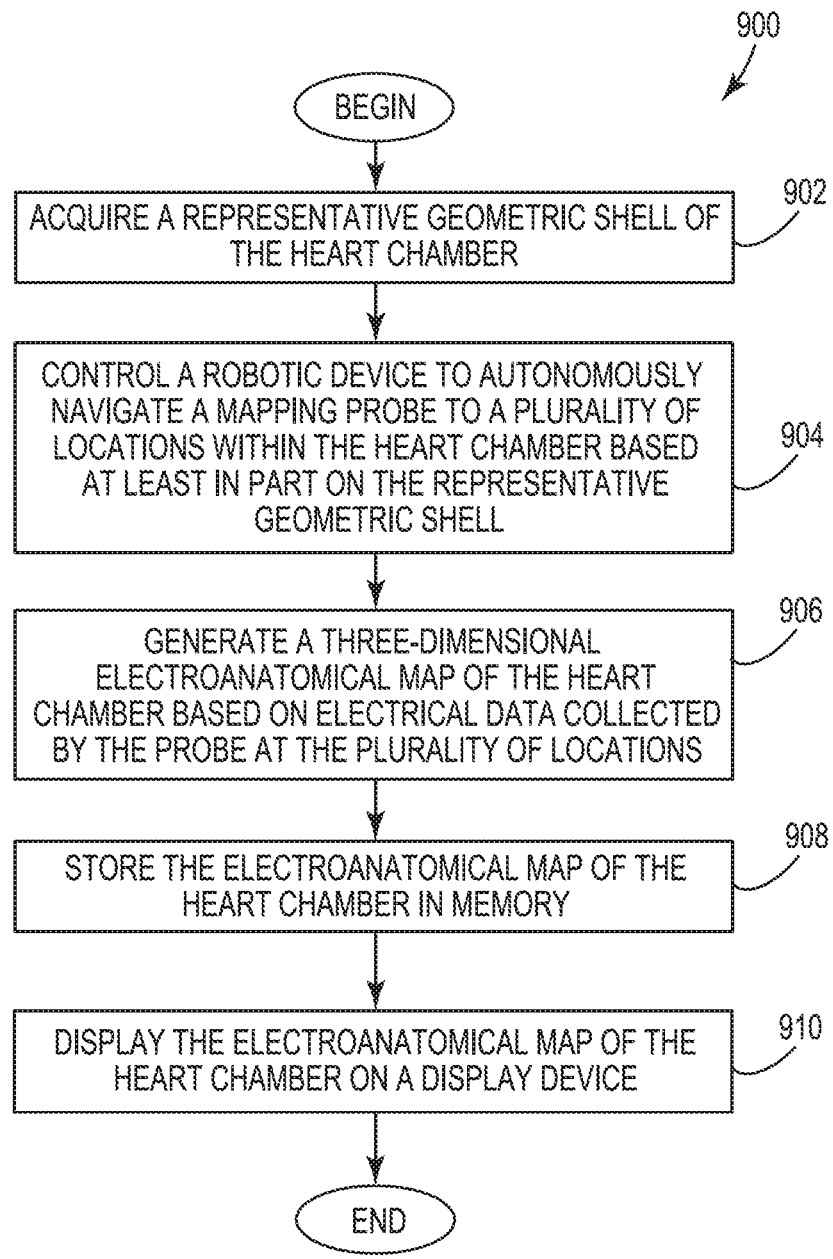
FIG. 9 is a flow diagram depicting an illustrative method of an autonomous mapping procedure using the navigation system of FIG. 1 in accordance with embodiments of the disclosed subject matter.

FIG. 9 is a flow diagram showing an exemplary method of autonomous mapping procedure using the navigation system 10. As disclosed herein, the system 10 is not particularly limited and can perform any of the methods described within the scope of this disclosure. In FIG. 9, a method 900 of performing the autonomous mapping procedure is shown using the system 10.

At block 902, the navigation processor 60 acquires the representative geometric shell 602 of the heart chamber 12 to start the mapping procedure based on the representative geometric shell 602. For example, the navigation processor 60 initially guides the mapping probe 14 within the heart chamber 12 using the representative geometric shell 602 as the initial reference.

At block 904, the navigation processor 60 controls the robotic device 62 to autonomously navigate the mapping probe 14 to a plurality of locations within the heart chamber 12 based at least in part on the representative geometric shell 602. For example, the navigation processor 60 utilizes a machine learning process or algorithm to generate a three-dimensional electroanatomical map of the heart chamber 12 while the autonomous navigation of the mapping probe 14 is performed in the heart chamber 12. As such, the navigation processor 60 relates the electroanatomical map of the heart chamber 12 to three-dimensional positional data corresponding to a plurality of anatomical locations of the heart chamber 12.

At block 906, using the machine learning process, the navigation processor 60 generates the three-dimensional electroanatomical map of the heart chamber 12 based on electrical data collected by the mapping probe 14 at the plurality of locations of the heart chamber 12. As discussed above, the machine learning process enables the navigation processor 60 to continuously and autonomously control the robotic device 62 beyond the portion of the heart chamber 12 defined by the representative geometric shell 602.

At block 908, the navigation processor 60 stores, e.g., in memory 61 (FIG. 1), the electroanatomical map of the heart chamber 12 corresponding to the plurality of anatomical locations of the heart chamber 12. In embodiments, the memory 61 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like.

In embodiments, the memory 61 stores computer-executable instructions for causing the navigation processor 60 and/or the processing system 32 to implement aspects of embodiments of system components discussed herein and/or to perform aspects of embodiments of methods and procedures discussed herein. The computer-executable instructions may include, for example, computer code, machine-useable instructions, and the like such as, for example, program components capable of being executed by one or more processors associated with the system 10. Program components may be programmed using any number of different programming environments, including various languages, development kits, frameworks, and/or the like. Some or all of the functionality contemplated herein may also, or alternatively, be implemented in hardware and/or firmware.

At block 910, the navigation processor 60 selectively displays a region associated with the electroanatomical map of the heart chamber 12. For example, a display device 40 (FIG. 1) is operatively coupled to the navigation processor 60 and/or the processing system 32, and is configured to display a three-dimensional graphical representation of the electroanatomical map of the heart chamber 12 on a screen or other suitable displays. For example, the device 40 can be a CRT, LED, or other type of display, or a printer. The device 40 presents the relevant characteristics in a format useful to the user.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for performing autonomous cardiac mapping of a heart chamber having an inner cardiac wall, the method comprising:
 acquiring a representative geometric shell of the heart chamber;
 controlling a robotic device to autonomously navigate a mapping probe, including an ultrasound transducer distance sensor, to a plurality of locations within the heart chamber based at least in part on the representative geometric shell; and
 generating a three-dimensional electroanatomical map of the heart chamber based on detecting at least a portion of the inner cardiac wall and collecting electrical data sensed by the mapping probe at the plurality of locations;
 wherein the ultrasound transducer senses a distance between the portion of the inner cardiac wall and the ultrasound transducer and navigating of the mapping probe is based on the distance sensed by the ultrasound transducer.

2. The method of claim 1, wherein the representative geometric shell comprises a template defining a generic geometry of the heart chamber.

3. The method of claim 1, wherein the representative geometric shell includes image information associated with the heart chamber based on at least one of: computerized tomography scan information, magnetic resonance imaging information, and ultrasound wave information.

4. The method of claim 1, wherein generating the electroanatomical map of the heart chamber comprises utilizing a machine learning process to generate the electroanatomical map of the heart chamber while the autonomous navigation of the mapping probe is performed in the heart chamber.

5. The method of claim 4, further comprising autonomously navigating the mapping probe within the heart chamber in real time based on the machine learning process independent of the representative geometric shell.

6. The method of claim 4, wherein the machine learning process uses data representative of at least one of: a mechanical feedback signal associated with the robotic device, an electrogram signal associated with the heart chamber, an impedance value associated with the heart chamber, a position tracking signal associated with the mapping probe, and the image information associated with the heart chamber.

7. The method of claim 1, wherein generating the electroanatomical map comprises relating the electroanatomical map of the heart chamber to three-dimensional positional data corresponding to the plurality of anatomical locations of the heart chamber.

8. The method of claim 1, further comprising storing, in memory, the electroanatomical map of the heart chamber corresponding to the plurality of anatomical locations of the heart chamber.

9. The method of claim 1, further comprising selectively displaying a region associated with the electroanatomical map of the heart chamber.

10. The method of claim 1, further comprising using a mechanical interface operatively coupled to the processor and the mapping probe having one or more electrodes coupled to a distal side of the mapping probe.

11. A system for autonomous cardiac mapping of a heart chamber having an inner cardiac wall, the system comprising:
    a processor being configured to:
        acquire a representative geometric shell of the heart chamber;
        control a robotic device to autonomously navigate a mapping probe, including an ultrasound transducer distance sensor, to a plurality of locations within the heart chamber based at least in part on the representative geometric shell; and
        generate a three-dimensional electroanatomical map of the heart chamber based on detecting at least a portion of the inner cardiac wall and collecting electrical data sensed by the mapping probe at the plurality of locations and using the ultrasound transducer to measure the distance between the portion of the inner cardiac wall of the heart chamber and the ultrasound transducer.

12. The system of claim 11, wherein the representative geometric shell comprises a template defining a generic geometry of the heart chamber.

13. The system of claim 11, wherein the representative geometric shell includes image information associated with the heart chamber based on at least one of: computerized tomography scan information, magnetic resonance imaging information, and ultrasound wave information.

14. The system of claim 11, wherein the processor is further configured to utilize a machine learning process to generate the electroanatomical map of the heart chamber while the autonomous navigation of the mapping probe is performed in the heart chamber.

15. The system of claim 11, wherein the processor is further configured to autonomously navigate the mapping probe within the heart chamber in real time based on the machine learning process independent of the representative geometric shell, and the machine learning process uses data representative of at least one of: a mechanical feedback signal associated with the robotic device, an electrogram signal associated with the heart chamber, an impedance value associated with the heart chamber, a position tracking signal associated with the mapping probe, and the image information associated with the heart chamber.

16. The system of claim 11, further comprising a mechanical interface operatively coupled to the processor and the mapping probe having one or more electrodes coupled to a distal side of the mapping probe.

* * * * *